United States Patent [19]

Thomas

[11] 4,003,241

[45] Jan. 18, 1977

[54] ACCELEROMETER METHOD OF INDICATING ROLLING RESISTANCE OF A VEHICLE

[75] Inventor: Paul Randolph Thomas, Erie, Pa.

[73] Assignee: General Electric Company, Erie, Pa.

[22] Filed: July 19, 1974

[21] Appl. No.: 490,129

[52] U.S. Cl. .................................. 73/9; 35/19 R
[51] Int. Cl.² .................................. G01N 3/56
[58] Field of Search .............. 73/9, 7, 8, 514, 382, 73/1 DV, 1 D, 146; 35/19 R

[56] References Cited

UNITED STATES PATENTS

| | | | |
|---|---|---|---|
| 1,317,072 | 9/1919 | Carlier | 73/517 R |
| 2,024,231 | 12/1935 | Klopsteg | 73/382 |
| 2,052,205 | 8/1936 | Baughman | 73/517 R |
| 2,198,278 | 4/1940 | Van der Heiden | 73/9 X |
| 2,603,885 | 7/1952 | Bates | 35/19 R |
| 2,838,009 | 6/1958 | Bonanno | 35/19 R |
| 3,187,552 | 6/1965 | Davies | 73/9 |
| 3,195,342 | 7/1965 | Bartelink | 73/9 |

*Primary Examiner*—Richard C. Queisser
*Assistant Examiner*—Daniel M. Yasich
*Attorney, Agent, or Firm*—Walter C. Bernkopf; Albert S. Richardson, Jr.

[57] ABSTRACT

A portable unit comprising a tiltable accelerometer is mounted on a vehicle which is allowed to coast on a plane and a reading is taken to provide an indication of vehicle rolling resistance without regard to terrain, slope, vehicle weight or speed. By proper precalibration of the accelerometer, it is possible to obtain the coefficient of friction directly from the accelerometer reading. Other values which may be directly obtained from the output of the accelerometer when it is properly recalibrated include accelerating rate and braking rate of a vehicle and grade of terrain.

2 Claims, 4 Drawing Figures

ACCELEROMETER METHOD OF INDICATING ROLLING RESISTANCE OF A VEHICLE

Background of the Disclosure

This invention relates generally to measuring devices and more particularly to a method of indicating the rolling resistance of a vehicle by the sensing of vehicle acceleration.

In the evaluation of a vehicle and propulsion system as for example a pneumatic tired truck, it is necessary to determine the rolling resistance, $F_R$ of the vehicle under various operating conditions. Rolling resistance is the force required to maintain the steady speed of a vehicle on a level operating surface, and is a product of W, the weight of the vehicle plus load, and $\mu$ the coefficient of rolling resistance. The coefficient of rolling resistance is a function of many things including the vehicle and drive train, type and condition of tires, wind resistance and the surface on which the vehicle is operated. Therefore in order to obtain a meaningful value, it is desirable to measure rolling resistance over the actual terrain of use and under normal conditions of operation.

A common method by which the coefficient of rolling resistance is determined is by using a towing vehicle and draw bar as shown in FIG. 1 and measuring the draw bar pull force to calculate the coefficient of rolling resistance. This method therefore requires the use of a towing vehicle and appropriate apparatus to accurately measure the draw bar pulling force. There is thus the requirement for a draw bar having sufficient sensitivity to be accurate on level terrain at constant speed, and yet rugged enough to withstand acceleration and uphill pulls. Also, the method is limited to periods of active towing since, without special provisions, draw bars are not adaptable to use with compressive loads. Further, in order to obtain accurate measurements it is necessary for the hitches on the towing and towed vehicles to be at the same height above the operational surface. Otherwise there will be included in the measurement additional forces which are exerted in lifting or pulling down the front end of the towed vehicle. On non-uniform surfaces it is impossible to avoid minor differences in levels of the two vehicles, and the resulting measurements are correspondingly inaccurate. It thus becomes necessary to take a number of readings and compute an average value to obtain the desired degree of accuracy.

It is therefore an object of this invention to provide an accurate measurement of the coefficient of rolling resistance for a moving vehicle.

Another object of this invention is the provision for measuring rolling resistance of a vehicle under actual operating conditions.

Yet another object of this invention is the provision for measuring the rolling resistance of a vehicle without the use of another vehicle.

Still another object of this invention is the provision for accurately measuring the rolling resistance of a vehicle during operation over a non-uniform surface.

A further object of this invention is the provision for a method which is capable of measuring rolling resistance of a moving vehicle regardless of the slope of the terrain over which it is moved.

An additional object of this invention is the provision for a simple, effective, and economical apparatus for measuring rolling resistance of a vehicle.

These objects and other features and advantages will become more readily apparent upon reference to the following description when taken in conjunction with the appended drawings.

SUMMARY OF THE INVENTION

Briefly, in accordance with one aspect of the invention an accelerometer is mounted to the vehicle with its longitudinal axis of sensitivity aligned in the direction of vehicle travel. The vehicle is caused to coast and the output of the accelerometer is indicated by an associated meter. Consequently the meter reading represents the coefficient of rolling resistance which is the sum of the acceleration due to gravity (slope of the terrain) and the acceleration or deceleration of the vehicle as it coasts.

By another aspect of the invention the meter is pre-calibrated by simply tilting the accelerometer through a known angle and adjusting the meter to read out the sine of that angle or a number proportional thereto. As a result, in operation the accelerometer direct measure of the coefficient of rolling resistance regardless of terrain, slope, vehicle weight, or speed. In this way a vehicle may be tested under normal operating conditions without the use of any other vehicle. The only equipment needed is a portable unit to be placed on the vehicle and comprising the accelerometer and the output metering mechanism.

By a further aspect of the invention with proper re-calibration of the device it can alternatively be used for simple and quick determinations of acceleration and braking rates of a vehicle.

In the drawings as hereinafter described a preferred embodiment is depicted; however, various other modifications and alternate constructions can be made thereto without departing from the true spirit and scope of the invention.

Description of the Preferred Embodiment

Figure 1:
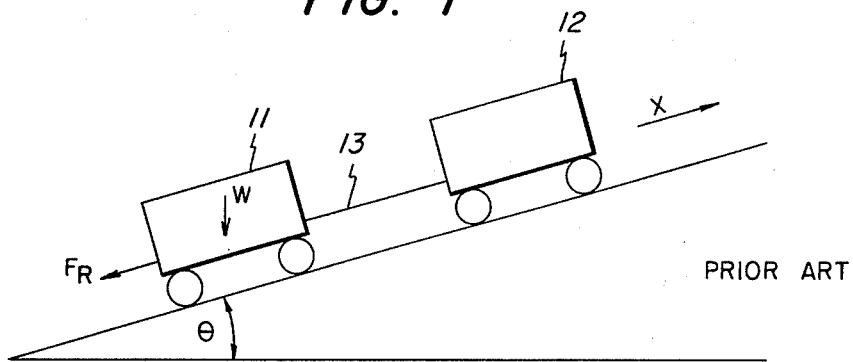
FIG. 1 is an illustration of a prior art method of measuring rolling resistance.

Referring now to FIG. 1 a prior art method of measuring rolling resistance, $F_R$, of a vehicle II is shown wherein a towing vehicle 12 is connected thereto by an instrumented draw-bar 13 to tow the vehicle II in the direction X on a plane inclined at $\theta°$ from the horizontal. The force equation may then be written as:

$$\text{Draw-bar Pull} = F_R + W \sin \theta + W\ddot{X}/g$$

where
$F_R$ = rolling resistance
$W$ = vehicle gross weight
$\theta$ = slope of the surface
$\ddot{X}$ = acceleration of the vehicle in the X direction
$g$ = acceleration of gravity The first term in the equation represents rolling resistance, the second term represents the force required to lift the vehicle up the slope and the third term is the accelerating force. Since the coefficient of rolling resistance $\mu = F_R/W$, then $$\mu = \text{Draw-bar Pull}/W - (\sin\theta + \ddot{X}/g)$$

If the surface is horizontal and a constant speed is maintained, then the only measurements which need to be made are those of draw-bar pull and vehicle weight. However, to achieve the desired accuracy, the draw-bar sensor must be reasonably sensitive and the vehicle hitches must be at the same level so as not to include the measurement the forces resulting from the lift or drag of the front end of the vehicle II. Further, a measurement taken under conditions of horizontal movement at a constant speed is difficult to conduct. For example, considering that a typical value of $\mu$ might be 0.03 and that arc sin 0.003 = 0.16 degrees, it can be seen that the surface must be perfectly flat or a substantial error will be introduced. Similarly, an acceleration of only 0.065 mph/sec will produce an error of 10 percent in the determination of the coefficient of rolling resistance. Further, the requirement for conducting the tests under these ideal conditions is undesirable since it is important that they be conducted under as close to actual operating conditions as possible.

It is therefore contemplate in this invention that the second part of the above equation be used and that the draw-bar pull of the above equation be allowed to go to zero so that the equation reduces to $\mu = -(\sin\theta + \ddot{X}/g)$. This is accomplished by removing the towing vehicle and draw-bar and allowing the test vehicle to coast.

Since the only measurements that need be taken are the slope of the test surface and the acceleration of the vehicle, the test may be conducted during normal operation of a vehicle on either a positive or negative grade and while the vehicle is either accelerating or decelerating.

Figure 2:
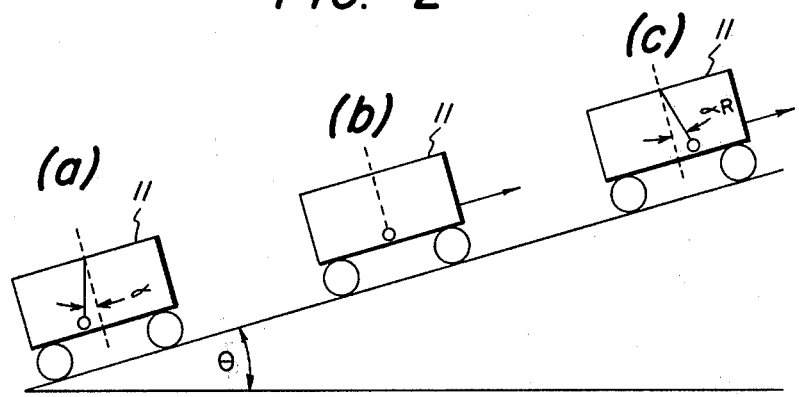
FIG. 2 shows a portable apparatus in accordance with the preferred embodiment of the invention.

A determination of the two unknowns can be made by a single measurement of vehicle acceleration under coasting conditions as is exemplified by the illustrations of FIG. 2. The vehicle shown, has installed thereon a seismic accelerometer which for small angles of inclination may be thought of as acting like a pendulum suspended from the vehicle. The angle $\alpha$ represents the departure of the pendulum from the vertical axis of a coordinate system on the vehicle and is caused by either the force of gravity, the acceleration of the vehicle on the slope, or both. In FIG. 2(a) the vehicle is stationary on the hill, $\alpha = \theta$, and the accelerometer reads $g\sin\theta$ in the direction shown. FIG. 2(b) shows the vehicle uphill with a theoretical rolling resistance of zero. Being theoretically frictionless, the coasting vehicle will decelerate at a rate $g\sin\theta$ and accelerometer reads $g\sin\theta$ due to slope minus $g\sin\theta$ due to deceleration, or zero. In FIG. 2(c) an actual vehicle is coasting uphill with a rolling resistance $F_R$. As a result the accelerometer pendulum is thrown forward on an angle $\alpha_R$ by the additional deceleration of the vehicle due to rolling resistance, and the sine of this angle thus provides an indication of the rolling resistance of the vehicle under those operating conditions. Similarly, an indication can also be obtained from a vehicle coasting on level ground or on a downhill grade. In this way the accelerometer acts as both an inclinometer and an accelerometer so as to provide a measure of $(\sin\theta + \ddot{X}/g)$, or the coefficient of rolling resistance when the vehicle is coasting without the use of the draw-bar. With the recent development of servo accelerometers the sensitivity and resolution capabilities allow for the measuring of 0.0005 $g$ which is well within the range expected for good accuracy in rolling resistance determination.

Because of the storage of energy in the rotating parts of a vehicle, such as wheels, gearing, and in the case of electric drive vehicles the motor armature, the vehicle will not accelerate or decelerate as rapidly as would be indicated from the preceeding discussion, and the measured values for $\mu$ will thus be smaller than the actual values. If, however, the geometry of the rotating part is known, then the rotating inertia can be calculated as a percentage of the total kinetic energy of the vehicle and expressed in terms of an equivalent value for gravitational acceleration used in calibration, thus giving a corrected direct reading device. For example, in the case of a large wheeled truck where the wheels are the principal rotating parts with respect to energy storage, the calculation is as follows:

$$\tfrac{1}{2}\frac{W}{g_{eq}}V^2 = \tfrac{1}{2}\frac{W}{g}V^2 + \tfrac{1}{2}I\omega^2$$

$$\frac{W}{g_{eq}}V^2 = \frac{W}{g}V^2 + I\frac{V^2}{R^2}$$

$$\frac{W}{g_{eq}} = \frac{W}{g} + \frac{I}{R^2}$$

$$g_{eq} = \frac{W}{\left(\frac{W}{g} + \frac{I}{R^2}\right)} = \text{equivalent } g$$

where:
$W$ = gross vehicle weight
$V$ = velocity
$I$ = polar moment of inertia
$W$ = angular velocity
$g$ = gravitational acceleration
$R$ = wheel radius
$g_{eq}$ = equivalent gravitational acceleration The equivalent value for gravitational acceleration as derived in the above equation is then applied to the final readings to adjust for error introduced. For example, in the use of a large truck the equivalent $g$ would come out to approximately 10% greater than 32 ft/sec², and therefore the final readings would have to be multiplied by 110 percent.

Alternatively, this correction can be applied in the calibration procedure so as to enable the direct reading of corrected values on the meter.

Figure 3:
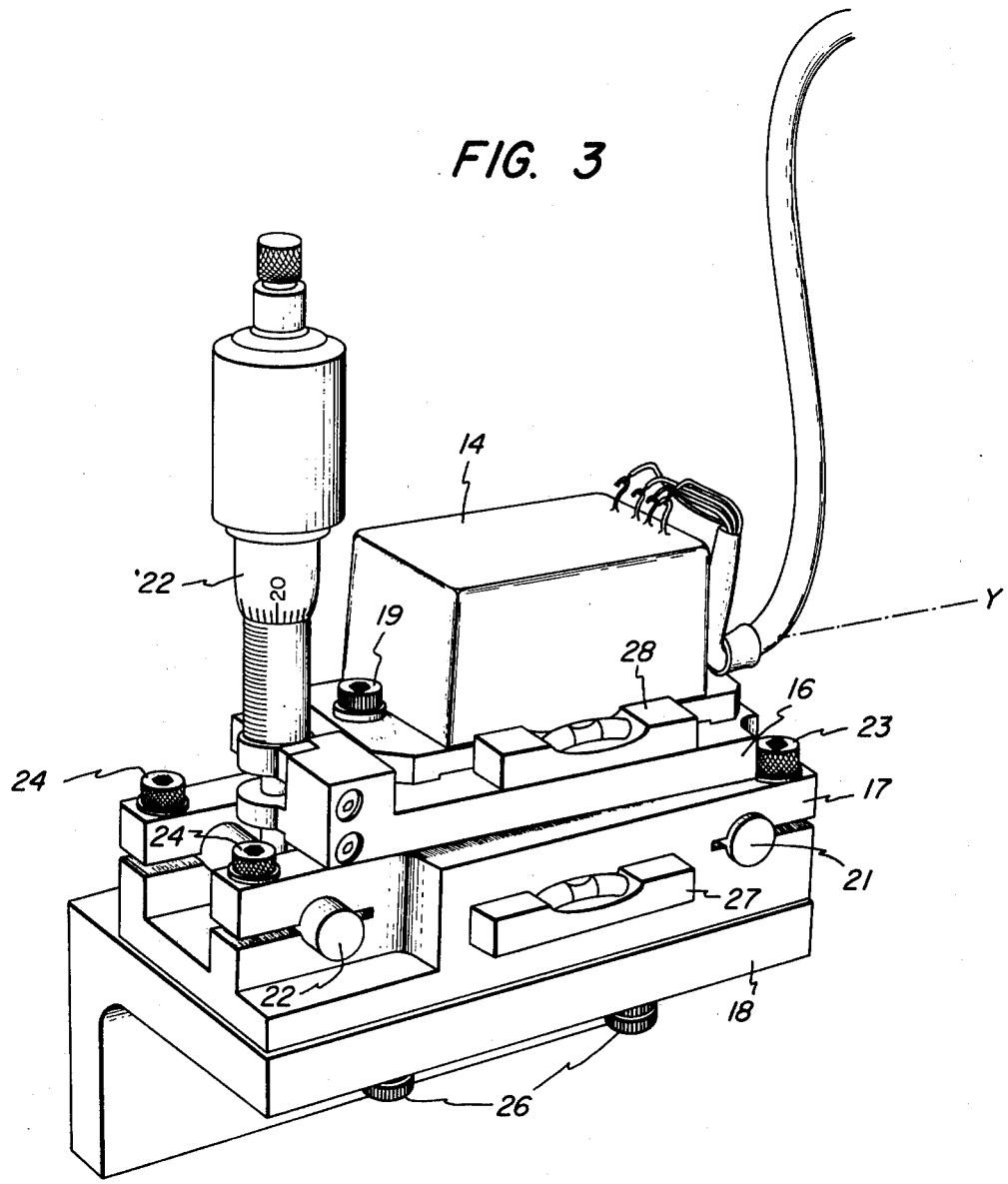
FIG. 3 is a plan view of the sensing portion of the invention.

The acceleration sensing device is a servo-accelerometer of a commercially available type and is designated by the numbers 14 in FIG. 3, with the associated assembly components including an adjustable table 16, a fixture base 17 and a sub-base 18. The accelerometer 14 is rigidly mounted to the adjustable table 16 by bolts 19, and the adjustable table 16 is in turn pivotably mounted at its one end to a pivot pin 21. Its other end is supported by a micrometer 22 mounted on the table with its adjustable shaft resting on a bearing pin 22 in the other end of the fixture base 17. Pivot clamp screws 23 act to adjust the clamping pressure on the pivot pin 21 and a similar pair of screws 24 act to secure the bearing pin 22 in the opposite end of the base. Finally, the fixture base 17 is rigidly secured by bolts 26 to the sub-base 18.

In a typical installation the expendable sub-base 18 is clamped or welded to a horizontally oriented vehicle frame with the long axis Y of the accelerometer parallel to the direction of vehicle travel. A bubble reference indicator 27 mounted to the fixture base 17 provides a ready means of installing the device in a level position on the vehicle. Any subsequent adjustments to accomplish final leveling can be made by movement of the micrometer 22 to tilt the table 16, with the bubble indicator 28 providing the final reference for accelerometer attitude. In the event that a true horizontal surface is not available for performance of the final leveling, zero may be taken as the mean of two micrometer readings when the device is leveled with the vehicle facing in opposite directions at the same location.

After the instrument has been leveled, calibration of the system is accomplished while the vehicle is standing still by adjusting the micrometer to tilt the accelerometer through a known angle with respect to horizontal according to Table I and then calibrating a meter connected to the accelerometer output by adjusting the meter setting to obtain the appropriate simulated rolling resistance reading. In Table 1, the coefficient of rolling resistance is indicated in the left-hand column in percentage units for the respective calibration angles which are listed in the Table. The indicated coefficient is thus seen to be related to the sine value of the selected calibration angle by a multiple of 100.

Table I

| (%) | Calibration Angle arc sin (100μ) | | Micrometer Division (MILS) |
|---|---|---|---|
| 1 | 0° | 34' | 34 |
| 2 | 1 | 9' | 69 |
| 3 | 1 | 43' | 103 |
| 4 | 2 | 17' | 137 |
| 5 | 2 | 52' | 172 |
| 6 | 3 | 26' | 206 |
| 8 | 4 | 35' | 275 |
| 10 | 5 | 44' | 344 |

Figure 4:
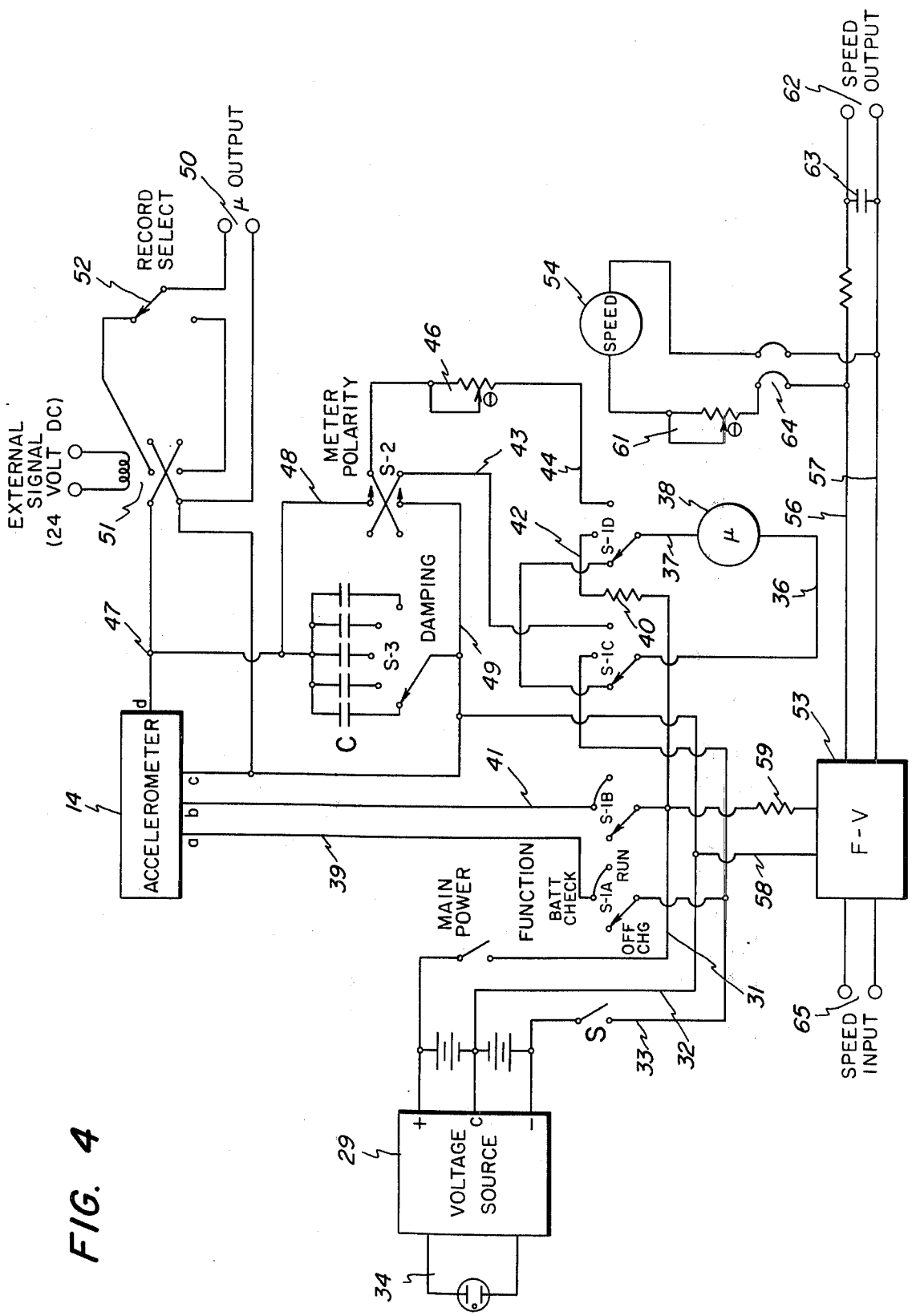
FIG. 4 is an electrical schematic diagram of the apparatus of the invention.

Referring now to FIG. 4 the power and metering circuitry is shown as it is connected to the accelerometer 14 in accordance with this invention. The accelerometer has terminals a, b, c and d representing the negative input, positive input, common, and output terminals respectively. Energization of the accelerometer comes from a d-c voltage source 29 having a positive lead 31, common lead 32, and negative lead 33, connected by a double throw switch main power switch S, which is used principally to isolate the power source when recharging it from an a-c source 34.

Connected between the voltage source 29 and the accelerometer 14 is a four-pole three-position function switch S-1 with the pole S-1A connected to the negative lead 33, and pole S-1B connected to the positive lead 31. Poles S-1C and S-1D are connected to lines 36 and 37, respectively, which in turn are connected to the two terminals of a meter 38 marked in arbitrary units for reading the accelerometer output. Looking at the three position alternatives of switch S-1, the left position represents the off condition when the meter is shorted and the accelerometer de-energized, the upper position is used for a battery check and the right position is used for the running or operation condition. At the S-1 pole, when it is in the off position an open circuit exists and while in either of the other two positions the pole is connected by a line 39 to the A terminal of the accelerometer. At the S-2 pole the circuit is open in the off position and when in either of the "battery check" or "run" positions the pole is connected to accelerometer terminal B by line 41, thereby providing a positive voltage thereto. Referring then to poles S-1C and S-1D, in the off position they are shorted by a line 42. In the battery check position, pole S-1C is connected to the negative lead 33, and pole S-1D is connected to the positive lead 34 to impose a voltage across the meter 38 and resistance 40. In the run position pole S-1C is connected by lead 43 to one output terminal of a reversing switch S-2 and pole S-1D is connected by lead 44 to the other output terminal thereof to thereby connect the meter to the accelerometer output. A calibrating potentiometer 46 is connected in line 44 to calibrate the meter 38 in accordance with the representative values of Table I. The reversing switch S-2 is used to select the meter polarity to accommodate either positive or negative acceleration readings with full scale deflection of the meter.

Referring again to the accelerometer 14, its terminal C is connected directly to the battery common lead 32 and its terminal D is an output terminal connected to output junction 47. One input terminal of reversing switch S-2 is connected to junction 47 by line 48 and the other is connected to the common lead by line 49. Connected between junction 47 and line 49 is a bank of parallel damping capacitors C for damping the accelerometer output. A switch S-3 is used to select the desired level of damping to eliminate deflections due to such forces as for example those caused by bumps in the roadway.

Since it is often desirable to monitor the accelerometer output on a continuous basis, the output terminals, designated by μ output, are provided between terminals C and D with a reversing relay 51 and a selector switch 52 connected therebetween. Since the accelerator reading is valid as a measure of the coefficient of rolling resistance only during periods of coasting operation, and since accelerating or braking rates can be determined only during those periods of operation, it is desirable to record data only during those intervals of time. The accelerometer output is therefore fed to an output jack through the 24V DPDT relay and the SPDT toggle switch in such a way that the output jack is shorted (zero output) whenever an externally applied 24V signal is present or absent, depending on the desired readings. For example, if the relay 51 is externally connected so as to be at 24 volts when the vehicle is coasting and 0 volts when the vehicle is not coasting, then the switch 52 is on in one position and off in the other. If the relay is connected to be energized under opposite conditions (vehicle not coasting) then the switch positions will be reversed. This combination provides the flexibility to ensure that the data is recorded only when the accelerator output is a valid signal, regardless of whether one is working with braking rates or with acceleration rates, or whether the external source energizes or de-energizes the reversing relay when operating in that condition.

When conducting tests for the determination of the coefficient of rolling resistance, it is desirable to also have a concurrent determination of vehicle speed. This can be accomplished by use of the same d-c power source 24 to energize an F-V converter 53 whose output is fed to a speed meter 54 along lines 56 and 57. The tachometer is a commercially available frequency-to-voltage converter energized by d-c lines 58 and 59 and having an a-c input whose frequency corresponds to vehicle speed. Typically an a-c tachometer generator or magnetic pickup is used to provide the speed input signal. The meter 54 is arbitrarily marked and is calibrated by adjusting the calibration potentiometer 61 to obtain the appropriate meter reading when using known speed input signal. For purposes of monitoring and recording a speed output jack 62 is provided to give continuous speed readings. A capacitor 63 is connected to provide damping but the output is not adjustably calibrated. Therefore, just as with the $\mu$ output jack, calibration is accomplished by using the recorder controls.

A d-c voltage proportional to speed may also be used as an input signal by removing the jumper links 64 and connecting the d-c source to the meter. This provides an isolated meter with a calibration adjustment to permit full scale deflection for d-c voltages up to a maximum level. Of course, the output jack 62 is disabled in this mode of operation.

Typically, the operation is as follows:

The accelerometer device is mounted on the vehicle in a manner described hereinbefore. The portable metering assembly is connected to the accelerometer as shown in FIG. 4. The main power switch S is closed and the function switch S-1 is set to the upper position to check the battery. The switch is then moved to the run position, and the meter 38 is calibrated by tilting the accelerometer in accordance with Table I using the micrometer screw and adjusting the potentiometer 46 such that the meter 38 reads in accordance with the prescribed values of Table I, or with those values as corrected by the use of the equivalent $g$ if the vehicle rotary inertia is considered to be significant. The vehicle is then made to coast and the coefficient of rolling resistance is read directly on the meter 38. Depending on whether the vehicle is going uphill or downhill the acceleration will be negative or positive. Accordingly, the reversing switch S-2 will have to be switched to the appropriate position to provide the proper polarity to the meter. Damping is adjusted as desired by selection of the proper position of switch S-3.

If recorded values are desired, the jack 50 is connected to a recorder and the recorder is calibrated to read in accordance with known values. To ensure that only valid values of acceleration readings are derived, the relay 51 is connected to the vehicle system in such a way as to be energized only when the vehicle is coasting. The selector switch 52 can then be appropriately operated to turn the system on or off.

At the same time the speed input terminals 65 may be connected to an a-c tachometer generator which is responsive to vehicle speed. The meter 54 is calibrated by setting of the potentiometer 61, and speed values are read directly on the meter 54. For recording these values the jack 62 is connected to the recorder which is appropriately calibrated by setting of the recorder controls.

What I claim as new and desire to secure by Letters Patent of the United States is:

1. A method of measuring rolling resistance of a vehicle comprising:
   a. adjustably mounting an accelerometer on a vehicle with its longitudinal axis of sensitivity aligned parallel with the direction of vehicle travel;
   b. connecting a meter to said accelerometer to be responsive to the signal output therefrom;
   c. calibrating said meter while the vehicle is stationary by inclining said accelerometer axis of sensitivity at a preselected small angle from the horizontal and adjusting the meter to read a multiple of the sine value of said angle; and
   d. allowing said vehicle to coast and reading the vehicle coefficient of rolling resistance directly from said meter while the vehicle is accelerating or decelerating.

2. A method of indicating rolling resistance of a vehicle comprising the steps of:
   a. allowing the vehicle to coast;
   b. providing on-board the vehicle an accelerometer which is arranged to derive an output signal the value of which is a measure of the difference between the rate of change of speed of the coasting vehicle due to the force of gravity and the actual rate of change of speed of the vehicle;
   c. indicating the value of said output signal; and
   d. proportioning the indicated value of said output signal so that it directly represents the coefficient of rolling resistance of the coasting vehicle, said proportioning step comprising:
      i. tilting the longitudinal axis of sensitivity of said accelerometer a known angle with respect to horizontal while the vehicle is standing still prior to allowing it to coast, and then
      ii. indicating that the value of the resulting output signal is a multiple of the sine of said angle.

* * * * *